United States Patent
Ogawa et al.

(10) Patent No.: US 9,086,388 B2
(45) Date of Patent: Jul. 21, 2015

(54) PATTERN EVALUATION METHOD AND APPARATUS

(71) Applicant: NuFlare Technology, Inc., Numazu-shi (JP)

(72) Inventors: Riki Ogawa, Kanagawa (JP); Nobutaka Kikuiri, Tokyo (JP)

(73) Assignee: NuFlare Technology, Inc., Numazu-shi (JP)

( * ) Notice: Subject to any disclaimer, the term of this patent is extended or adjusted under 35 U.S.C. 154(b) by 159 days.

(21) Appl. No.: 14/020,217

(22) Filed: Sep. 6, 2013

(65) Prior Publication Data
US 2014/0072202 A1    Mar. 13, 2014

(30) Foreign Application Priority Data
Sep. 11, 2012  (JP) .................. 2012-199366

(51) Int. Cl.
| | | |
|---|---|---|
| G06K 9/00 | (2006.01) | |
| G01N 21/95 | (2006.01) | |
| G01N 21/956 | (2006.01) | |

(52) U.S. Cl.
CPC .......... *G01N 21/9501* (2013.01); *G01N 21/956* (2013.01); *G01N 2021/95676* (2013.01)

(58) Field of Classification Search
USPC ................................................ 382/141–152
See application file for complete search history.

(56) References Cited

U.S. PATENT DOCUMENTS

| | | | | |
|---|---|---|---|---|
| 4,477,926 A | * | 10/1984 | Linger et al. ................. | 382/149 |
| 5,272,761 A | * | 12/1993 | Kanai et al. ................... | 382/147 |
| 5,442,714 A | * | 8/1995 | Iguchi .......................... | 382/144 |
| 5,513,275 A | * | 4/1996 | Khalaj et al. .................. | 382/149 |
| 6,072,897 A | * | 6/2000 | Greenberg et al. ........... | 382/144 |
| 6,137,901 A | * | 10/2000 | Harazaki ....................... | 382/144 |
| 7,366,620 B2 | * | 4/2008 | Yamaguchi et al. ........... | 702/40 |
| 2002/0006562 A1 | * | 1/2002 | Akutagawa et al. ............ | 430/30 |
| 2002/0012861 A1 | * | 1/2002 | Luhn et al. ..................... | 430/30 |

(Continued)

FOREIGN PATENT DOCUMENTS

| | | |
|---|---|---|
| JP | 2001-175857 A | 6/2001 |
| JP | 4236825 | 12/2008 |

(Continued)

OTHER PUBLICATIONS

U.S. Appl. No. 14/153,199, filed Jan. 13, 2014, Ogawa, et al.

(Continued)

*Primary Examiner* — Alex Liew
(74) *Attorney, Agent, or Firm* — Oblon, McClelland, Maier & Neustadt, L.L.P.

(57) ABSTRACT

A pattern evaluation method comprising the steps of, illuminating light from a light source constituting an optical system and acquiring an optical image of a sample having a repeated pattern with a period not more than a resolution of the optical system, allocating a gradation value to each pixel of the optical image and obtaining at least one of an average gradation value for each predetermined unit region and deviation of the gradation value in the unit region, and performing at least one of a process of converting the average gradation value into average line width information in the region of the repeated pattern and a process of converting the deviation of the gradation value into roughness of the repeated pattern and creating a map representing distribution of at least one of the average line width information and the roughness with the use of an obtained converted value.

11 Claims, 7 Drawing Sheets

(56) References Cited

U.S. PATENT DOCUMENTS

| | | | |
|---|---|---|---|
| 2003/0170552 A1* | 9/2003 | Miyashita et al. | 430/30 |
| 2004/0018436 A1* | 1/2004 | Ishikawa | 430/5 |
| 2004/0264759 A1* | 12/2004 | Hattori et al. | 382/145 |
| 2005/0048379 A1* | 3/2005 | Koehle et al. | 430/5 |
| 2006/0245636 A1* | 11/2006 | Kitamura et al. | 382/149 |
| 2008/0099676 A1* | 5/2008 | Sasajima et al. | 250/307 |
| 2008/0130982 A1* | 6/2008 | Kitamura et al. | 382/144 |
| 2010/0158345 A1* | 6/2010 | Kitamura et al. | 382/145 |
| 2010/0215247 A1* | 8/2010 | Kitamura et al. | 382/149 |
| 2011/0176719 A1* | 7/2011 | Inoue et al. | 382/149 |
| 2012/0140060 A1* | 6/2012 | Tsuchiya et al. | 348/126 |
| 2014/0218642 A1* | 8/2014 | Iwami | 349/12 |

FOREIGN PATENT DOCUMENTS

| | | |
|---|---|---|
| JP | 2012-145334 A | 8/2012 |
| KR | 10-2010-0029781 A | 3/2010 |

OTHER PUBLICATIONS

Office Action issued Aug. 22, 2014 in Korean Patent Application No. 10-2013-0101672 (with English language translation).

U.S. Appl. No. 13/968,816, filed Aug. 16, 2013, Shinji Sugihara, et al.

* cited by examiner

PATTERN EVALUATION METHOD AND APPARATUS

CROSS-REFERENCE TO THE RELATED APPLICATION

The entire disclosure of the Japanese Patent Application No. 2012-199366, filed on Sep. 11, 2012 including specification, claims, drawings, and summary, on which the Convention priority of the present application is based, are incorporated herein in its entirety.

FIELD OF THE INVENTION

This invention relates to a Pattern Evaluation Method and Apparatus.

BACKGROUND

In a large scale integration (LSI), as the degree of integration and the capacity are increased, the circuit size required for a semiconductor device has been gradually narrowing. In the manufacture of the semiconductor device, a pattern is exposed and transferred onto a wafer by a reduced projection exposure apparatus generally called a stepper or scanner to form a circuit, using an original image pattern (meaning a mask or a reticle and hereinafter collectively referred to as a mask) formed with a circuit pattern, whereby the semiconductor device is manufactured.

Enhancement of yield is essential, as the manufacture of LSI involves a large manufacturing cost. Meanwhile, recent typical logic devices are under such a condition that the formation of a pattern with a line width of several ten nm is required. In these circumstances, shape defects of a pattern of a mask constitute a major cause of reduction in the yield. More specifically, the shape defect of the mask pattern includes, for example, roughness of the pattern edge (edge roughness), a line width abnormality in the pattern, and a gap abnormality between a target pattern and a pattern adjacent thereto due to pattern positional deviation.

Along with miniaturization of an LSI pattern dimension formed on a semiconductor wafer, the size of the pattern defect of a mask is also miniaturized. The dimensional accuracy of the mask is enhanced, whereby the deviation of the process terms and conditions is to be absorbed, and thus, in the inspection of a mask, an extremely small pattern is required to be detected. As a result, high inspection accuracy is required of an apparatus, which evaluates a pattern of a mask used for transfer in the manufacture of LSI. As seen in Patent document 1 (U.S. Pat. No. 4,236,825) an Inspection Apparatus for detecting a fine defect on a mask is disclosed.

Recently, as a technique for forming a fine pattern, nanoimprint lithography (NIL) has attracted attention. In this technique, a mold (die) having a nanoscale microstructure is pressure applied to a resist on a wafer to form the fine pattern on the resist.

In the nanoimprint technology, to increase productivity, a plurality of duplicate templates (replica templates) is produced using a master template as an original plate, and each replica template is mounted in different nanoimprint apparatuses during use. The replica template is required to be produced so as to accurately correspond to the master template. Thus, high inspection accuracy is required when the master template is evaluated. Further, high inspection accuracy is also required when the replica template is evaluated.

A mask is generally formed to have a size four times larger than a circuit size. A pattern is reduced and exposed onto a resist on a wafer by a reduced projection exposure device, using this mask, and thereafter, the pattern is developed to thereby form a circuit pattern of a semiconductor. Meanwhile, a template in nanoimprint lithography is formed to have a size the same as the circuit size. Thus, a shape defect in a pattern of the temperate has a higher degree of influence on a pattern to be transferred onto the wafer than the shape defect in the pattern of the mask. Accordingly, a pattern defect of the template is required to be evaluated with higher accuracy than the evaluation of the pattern defect of the mask.

However, these days when a circuit pattern is being miniaturized, the pattern size is becoming more minute than the resolution of an optical unit in a pattern evaluation apparatus. For example, in a dense pattern in which a line width of the pattern formed on a template is not more than 40 nm, the pattern cannot be resolved by a light source using DUV (Deep Ultraviolet radiation) light being 190-200 nm, even though this DUV light is easily created by an optical unit. Thus, although a light source using EB (Electron Beam) is used, throughput is low, and a problem arises in that the light source cannot be mass-produced.

The present invention has been made in consideration of the above points. Namely, this invention provides a pattern evaluation method and a pattern evaluation apparatus, which can evaluate a fine pattern with high accuracy without inducing reduction in throughput.

Other challenges and advantages of the present invention are apparent from the following description.

SUMMARY OF THE INVENTION

According to one aspect of the present invention, a pattern evaluation method comprising, illuminating light from a light source constituting an optical system and acquiring an optical image of a sample having a repeated pattern with a period not more than a resolution of the optical system, allocating a gradation value to each pixel of the optical image and obtaining at least one of an average gradation value for each predetermined unit region and deviation of the gradation value in the unit region, and performing at least one of a process of converting the average gradation value into average line width information in the unit region of the repeated pattern and a process of converting the deviation of the gradation value into roughness of the repeated pattern and creating a map representing distribution of at least one of the average line width information and the roughness with the use of an obtained converted value.

Further to this aspect of the present invention, a pattern evaluation method, wherein a wavelength of the light is longer by twice or more than a pitch of the repeated pattern.

Further to this aspect of the present invention, a pattern evaluation method, wherein the light is deep ultraviolet radiation.

Further to this aspect of the present invention, a pattern evaluation method, wherein the repeated pattern is a line-and-space pattern, and the average line width information is an average value of a plurality of widths of a line of the line-and-space pattern.

Further to this aspect of the present invention, a pattern evaluation method, wherein the repeated pattern is a line-and-space pattern, and the roughness is a line edge roughness which is a size of irregularities on sidewalls of the line.

Further to this aspect of the present invention, a pattern evaluation method, wherein the repeated pattern is a line-and-space pattern, and the design width of a line is not more than 40 nm.

In another aspect of the present invention, a pattern evaluation apparatus comprising, an optical image acquiring unit which acquires an optical image of a pattern, which is a target to be evaluated, with the use of an image sensor, an optical image processing unit which allocates a gradation value to each pixel of the optical image and obtains at least one of, an average gradation value for each predetermined unit region, and deviation of the gradation value in the unit region, and a map creating unit which performs at least one of a process of converting the average gradation value into average line width information in the unit region of the pattern and a process of converting the deviation of the gradation value into roughness of the pattern and creates a map representing distribution of at least one of the average line width information and the roughness, using an obtained converted value, wherein the optical image acquiring unit comprises a light source illuminating light to the pattern and a lens focusing light from the light source, transmitted through or reflected by the pattern, on the image sensor, and a resolution limit determined by a wavelength of the light from the light source and the numerical aperture of the lens is a value that does not resolve the pattern.

Further to this aspect of the present invention, a pattern evaluation apparatus, wherein the light from the light source has a wavelength longer by twice or more than a pitch of the pattern.

Further to this aspect of the present invention, a pattern evaluation apparatus, wherein the light from the light source is deep ultraviolet radiation.

Further to this aspect of the present invention, a pattern evaluation apparatus, further comprising a comparing unit which compares the optical image with a reference image and determines that there is a defect when a difference value between the optical image and the reference image exceeds a predetermined threshold value.

Further to this aspect of the present invention, a pattern evaluation apparatus, wherein the reference image is a reference image created from design data of the pattern, the apparatus further comprising a reference image creating unit which creates the reference image, wherein the reference image created by the reference image creating unit is sent to the comparing unit.

DETAILED DESCRIPTION OF THE EMBODIMENTS

Many of the patterns formed on a wafer are repeated patterns such as a line-and-space pattern, that is, a regular pattern repeated with a periodicity. Accordingly, such a repeated pattern is formed on a template used in the nanoimprint lithography.

When a dense pattern whose line width is not more than 40 nm is to be formed by an optical unit using DUV light, even if a lens (numerical aperture NA=1) of theoretical limitation is used, this pattern cannot be resolved. However, when such a pattern is a repeated pattern, if edge roughness increases in a part of the pattern, or if a part of the pattern is lacking, the regularity is disturbed and changes the gradation value of an optical image.

Figure 1:
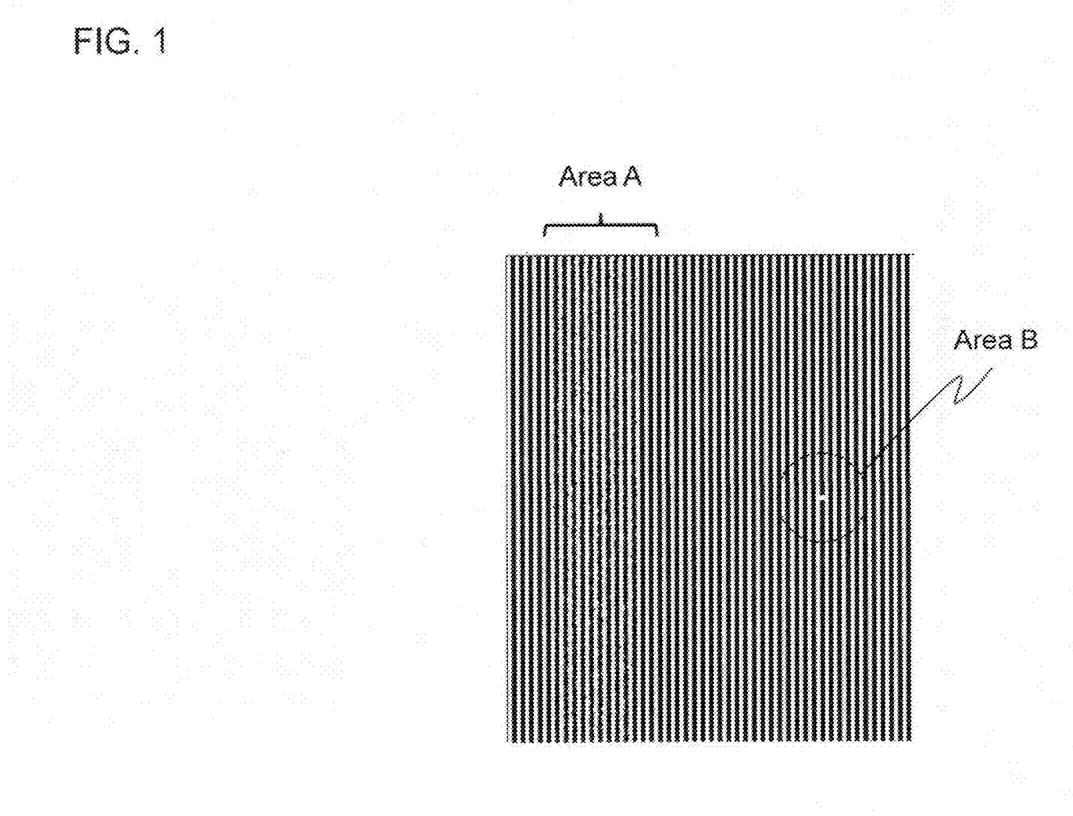
FIG. 1 is an example of a line and space pattern.

FIG. 1 is an example of a line and space pattern. In FIG. 1, the size of the pattern is assumed to be smaller than a resolution limit of an optical system.

In the region A of FIG. 1, pattern edge roughness is increased. Meanwhile, in the region B, a part of the line pattern is lacking.

Figure 2:
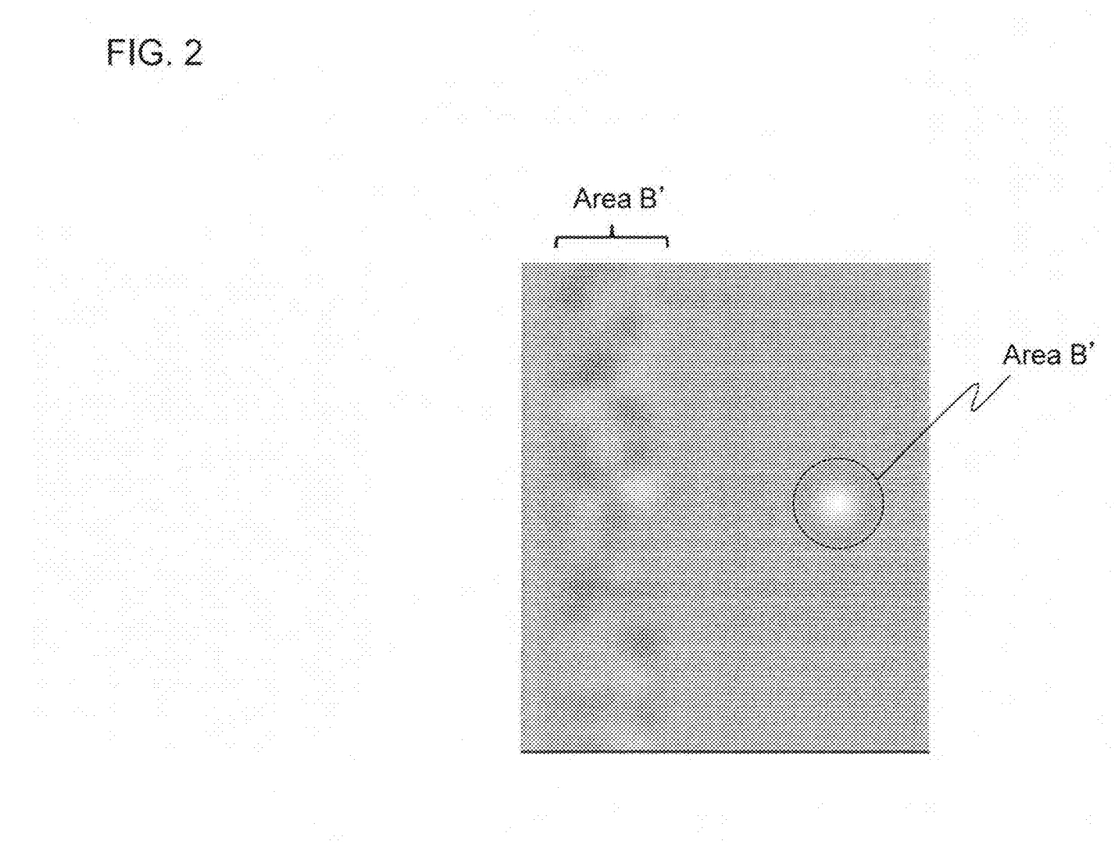
FIG. 2 shows an optical image of the pattern of FIG. 1 obtained by simulation.

FIG. 2 shows an optical image of the pattern of FIG. 1 obtained by simulation. In FIG. 2, although the pattern is not resolved, it is found that regions having different gradation values from the periphery are located at positions (regions A' and B') corresponding to the shape defects of FIG. 1.

As described above, even in a line-and-space pattern having a line width narrower than the resolution limit of the optical system, if there is edge roughness and the shape defect due to a lack in the pattern, the regularity of the pattern is disturbed, and as a result, a gradation value of a portion having the shape defect is different from the gradation values of the periphery of the portion. This feature can be used to calculate the degree of the edge roughness and detection of the presence or absence of the shape defect due to the lack in the pattern. The edge roughness occurs in a process for pattern formation such as drawing and etching. Accordingly, when the degree of the roughness and an in-plane distribution of the degree of the roughness are acquired, it is useful in that the degree of the roughness and the in-plane distribution of the degree of the roughness can be fed back to setting of conditions of the drawing process and the etching process. In this invention, the degree of the roughness is measured throughout the whole template, and the distribution of the roughness can be displayed.

Meanwhile, even in a regular pattern whose regularity is not disturbed, a ratio of a line and a space in a line-and-space pattern can be measured by measuring an average gradation value of the pattern. In this case, the cause of change of the gradation value can be considered as follows.

A pattern formed on a template for nanoimprinting is formed by minute roughness having a depth of several ten nm for the purpose of transferring the pattern with a mold. The reflectance of light applied to the line-and-space that has such a shape and is not more than the resolution limit is attenuated or enhanced by interference between reflected light from a dug region (space) and reflected light from a remaining region (space). However, when the ratio of the line and the space changes to be shifted to either the line or the space, an interference effect is reduced, and the reflectance approaches the value obtained upon Fresnel reflection. In extreme situations in which the space is 100% or the line is 100%, the reflectance is equal to the value of the Fresnel reflection.

As described above, in the line-and-space pattern, the amount of reflected light is changed depending on the ratio of the line. Since the line and the space have a front and rear relationship, it can be said that the amount of reflected light is changed depending on the ratio of the space. The use of such features allows calculation of the ratio of the line and the space in the line-and-space pattern.

In a process for producing a template, a pattern pitch accuracy depends only on the performance of a drawing apparatus. Meanwhile, a line width accuracy depends on processes such as etching. Accordingly, the pattern pitch accuracy is higher than the line width accuracy and can be regarded as a fixed value. This fact means that the line width is represented by the ratio of the line and the space. Since the line and the space are formed in the pattern formation process such as drawing and etching, the actual line width is created by the pattern formation process. Thus, it is useful in terms of reduction of defects to determine the in-plane distribution of the line width and feed back the in-plane distribution to the drawing process and the etching process. In this invention, line width information obtained from the average gradation value is measured throughout the template, and the distribution can be displayed.

Next, a pattern evaluation method according to the present embodiment will be described in detail. The evaluation is performed with respect to uniformity of a pattern. Namely, how much the pattern is uniformly formed is evaluated based on roughness of the pattern edge, a lack in the pattern, the line width abnormality in the pattern, or a degree of the positional deviation of the pattern. The above optical system is hereinafter referred to as an observation optical system.

Firstly, an optical image of a sample to be evaluated will be acquired.

The sample to be evaluated has a line-and-space pattern as a repeated pattern. For example, the sample is illuminated with light from a light source disposed above the sample. The light emitted from the light source preferably has a wavelength longer by twice or more than a pattern pitch. An objective lens, a photodiode array (consisting of image sensors), and a sensor circuit are arranged under the sample, and the light transmitted through the sample is formed as an optical image on the photodiode array through the objective lens. The observation optical system is constituted of the light source, the objective lens, the photodiode array, and the sensor circuit. The resolution limit ($R=\lambda/2NA$) determined by the wavelength ($\lambda$) of the light from the light source and the numerical aperture (NA) of the objective lens is a value that does not resolve a pattern formed on the sample to be evaluated. In the magnification of the optical system, it is preferable that the size of one pixel is equal to or less than the resolution limit when one pixel of the photodiode array is converted into the size on a template. Consequently, roughness measurement accuracy can be maximally enhanced.

In this embodiment, light is illuminated from under the sample to be evaluated, and reflected light may then be focused on the photodiode array by a lens.

Pixel data in an optical image is represented by the gradation value of each pixel. For example, any of gradation values 0 to 255 from a gray scale having 256 stages of gradation values is allocated to each pixel. In this embodiment, an region to be evaluated of the sample is divided into predetermined unit regions, and the average gradation value in each unit region is obtained. The predetermined unit region may have a size of 1 mm×1 mm, for example.

Subsequently, the average gradation value in each unit region is calculated. For example, it is assumed that a width and a gap of each line in the sample to be evaluated are uniform. In this case, the average gradation value in each unit region is a uniform value. On the other hand, the line width of the line in a specific region is averagely narrowed or widened; for example, the average gradation value is changed depending on the line width. Thus, the calculated average gradation value is converted into average line width information, and the in-plane distribution of the line width in the template is output.

When deviation of the gradation value in each unit region is examined, the degree of the irregularities (roughness) of the pattern edge can be measured. When the pattern edge has no irregularity, the gradation value does not deviate. On the other hand, when the pattern edge has roughness, the gradation value deviates. Since standard deviation of the gradation value is proportional to standard deviation of the roughness of the pattern edge, the standard deviation of the roughness of the pattern edge can be calculated by obtaining the standard deviation of the gradation value. Consequently, the template in-plane distribution of the standard deviation calculated in each unit region can be output.

In the evaluation method according to the present embodiment, a map representing at least one of the distribution of the line width of a pattern and the distribution of the roughness of a pattern edge is created from the gradation value for each pixel in an optical image and the average gradation value of each unit region virtually dividing the region to be evaluated. More specifically, for a predetermined pattern, a value of the line width measured by dimension SEM and the gradation value of the optical image of the pattern are obtained to thereby establish a relational formula between the line width and the gradation value. Then, the average gradation value obtained from the optical image to be evaluated is converted into an average value of the line width in the unit region, using the relational formula. In this manner, the deviation of the gradation value, that is, the standard deviation of the gradation value is converted into the roughness of the pattern edge. The roughness is a line edge roughness which is a size of irregularities on sidewalls of the line. The fine irregularities of both edges of a line of a line-and-space pattern are measured by the cross-section SEM, and then the line edge roughness is obtained by calculating an average of the peak to peak values of each edge. Subsequently, the map representing at least one of the distribution of the average value of the line width and the distribution of the roughness of the pattern edge is created using a converted value.

The creation of the map allows the degree of the uniformity of the pattern on the sample to be known. Then, when it is determined that the line width and the roughness of the pattern edge are significantly varied, this information is fed back to the conditions of photolithography upon pattern formation, and exposure conditions and etching conditions for a resist can be optimized so that the variation is reduced.

Next, a pattern evaluation apparatus according to the present embodiment will be described.

Figure 3:
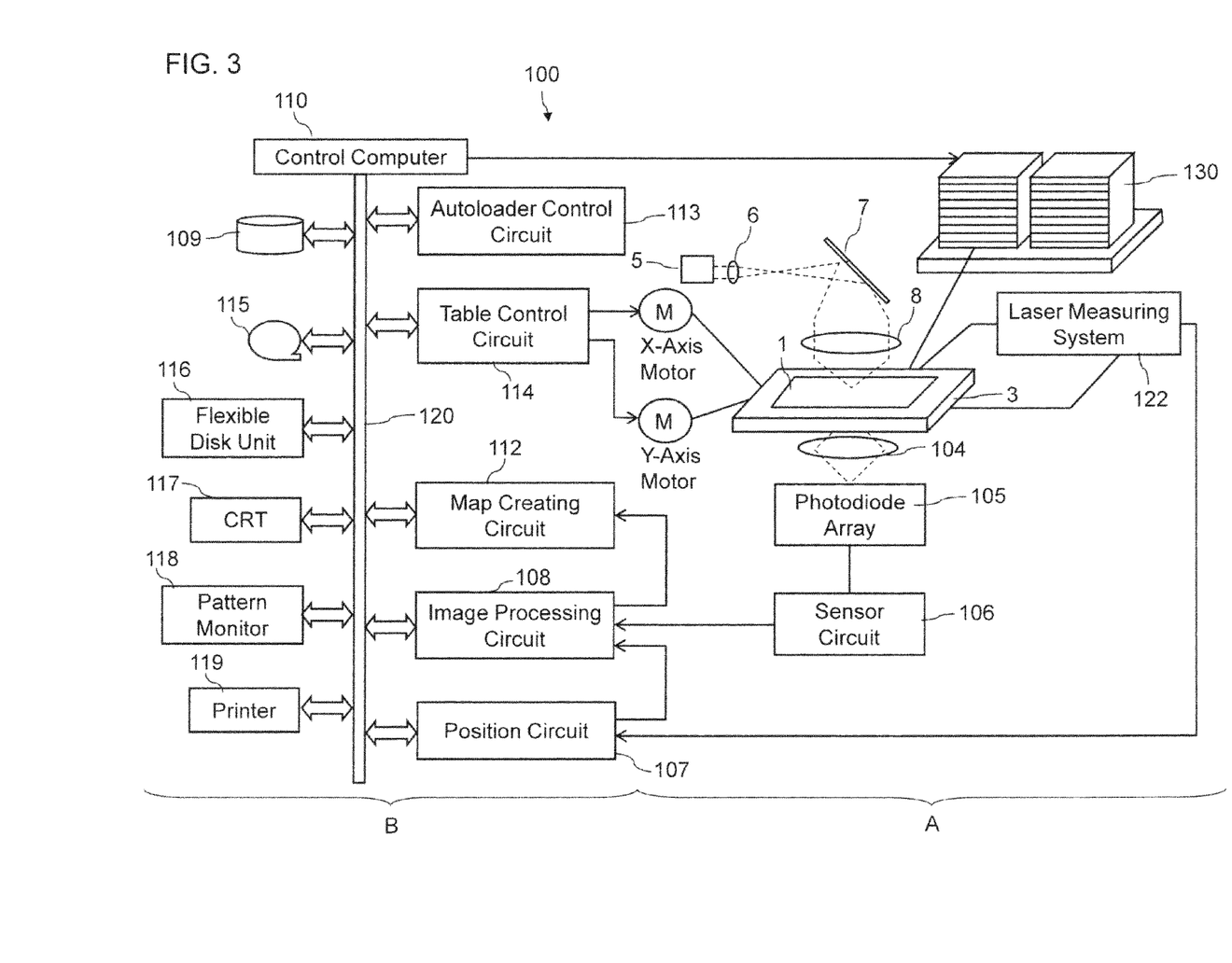
FIG. 3 is a diagram of a pattern evaluation apparatus according to the present embodiment.

FIG. 3 is a diagram of a pattern evaluation apparatus according to the present embodiment. As illustrated in FIG. 3, the pattern evaluation apparatus 100 includes an optical image acquisition unit A and a control unit B.

The optical image acquisition unit A has an observation optical system including a first light source 5, a lens 6, a lens 8, a lens 104, a mirror 7, a photodiode array 105, and a sensor circuit 106. Further the optical image acquisition unit A includes a XY table 3 movable in the horizontal direction (X and Y directions), a laser length measurement system 122, and an autoloader 130. The XY table 3 may be a structure capable of moving in a rotational direction (θ direction).

A sample 1 to be evaluated is placed on a Z table (not illustrated) movable in a vertical direction. The Z table is provided on the XY table 3, and can be moved in the horizontal direction by the XY table 3. In the sample 1, a repeated pattern such as a line-and-space pattern, that is, a regular pattern repeated with a periodicity is formed. The sample 1 includes, for example, a template used in the nanoimprint technology.

It is preferable that supporting members provided on the Z table 2 supports the sample 1 at three points. When the sample 1 is supported at four points, the height of the supporting member is required to be adjusted with higher accuracy. If the height adjustment is insufficient, the sample 1 may be deformed. On the contrary, using the three-point support, the sample 1 can be supported while the deformation of the sample 1 is suppressed to a minimum. For example, the supporting member is constituted using a ballpoint having a spherical head surface. Two of the three supporting members are in contact with the sample 1 at the adjacent two corners which are not opposing corners of four corners of the sample 1. In this case, the remaining one supporting member is disposed in a region between the two corners where the other two supporting members are not arranged.

The observation optical system described above is arranged above and under the sample 1. A resolution limit ($R=\lambda/2NA$) determined by the resolution limit of the optical unit, that is, a wavelength ($\lambda$) of light from the light source 5 and the numerical aperture (NA) of the lens 104 is a value in which a pattern formed in the sample 1 cannot be resolved.

In the observation optical system, the light source 5 illuminates light, used for evaluation, to the sample 1. The wavelength of the light emitted from the light source 5 is twice the size or more than twice the size of the pattern pitch. A pattern evaluation apparatus 100 is suitable for evaluation of a fine pattern having a line width of not more than 40 nm, and as the light source 5, a light source which illuminates DUV (Deep Ultraviolet radiation) light is preferably used. When the DUV light is used, a fine pattern can be evaluated with higher throughput than in the case of using EB (Electron Beam).

The light emitted from the light source 5 is transmitted through a lens 6 and the direction of light is changed by a mirror 7, and thus, is focused on the sample 1 by a lens 8. A photodiode array 105 is disposed under the sample 1, and light transmitted through the sample 1 is imaged on the photodiode array 105 by the lens 104, so that an optical image (to be described later) is generated.

In this embodiment, light may be illuminated from under the sample 1, and reflected light then focused on the photodiode array 105 by a lens.

Figure 4:
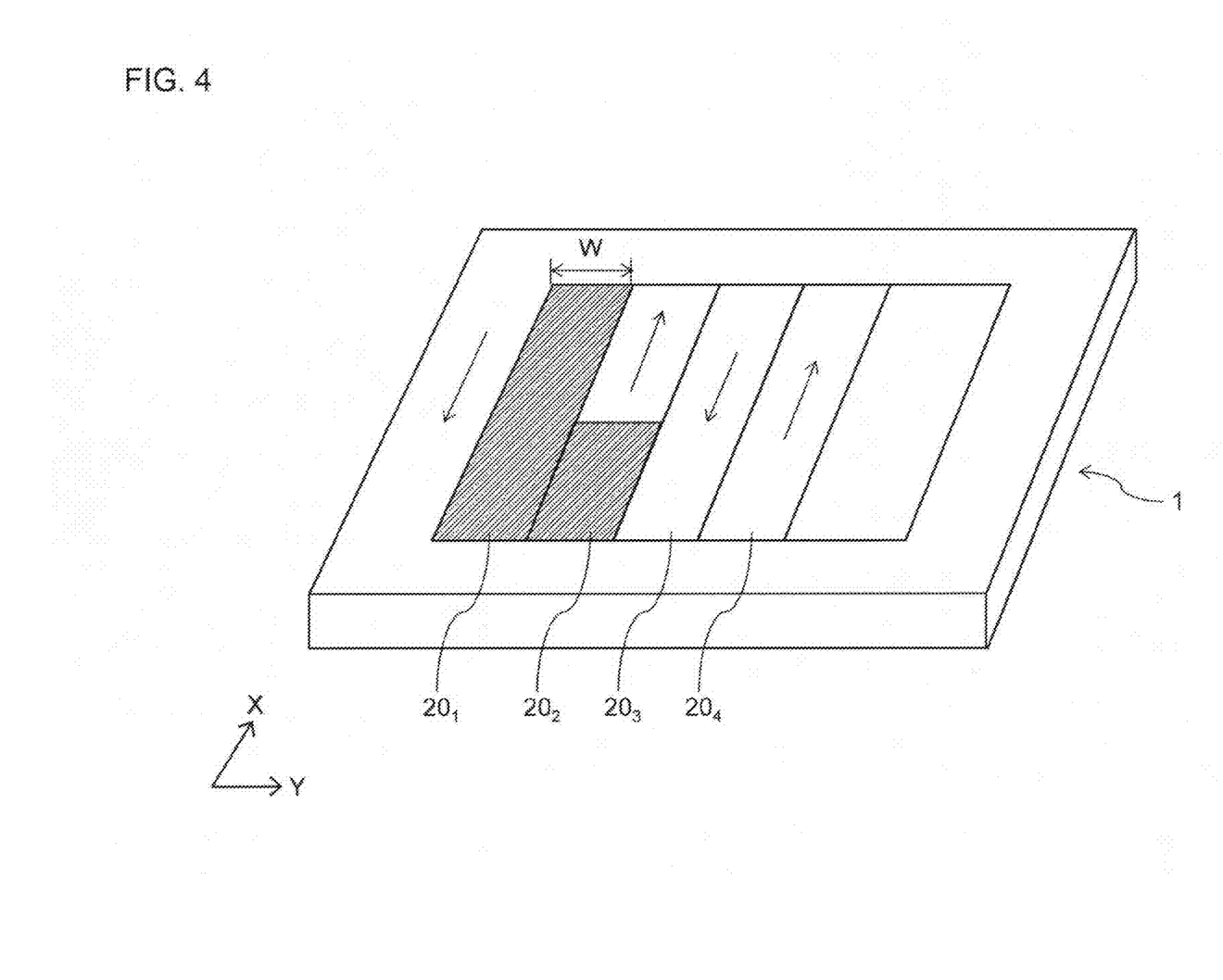
FIG. 4 is a diagram illustrating the way in which an optical image used is acquired.

FIG. 4 is a diagram illustrating the way in which an optical image used for evaluating the shape defects of patterns formed on the sample 1 is acquired.

As illustrated in FIG. 4, the region to be evaluated of the sample 1 is virtually divided into a plurality of strip-shaped frames 201, 202, 203, 204, etc., and the operation of the XY table 3 of FIG. 3 is controlled so that the respective divided frames $20_1$, $20_2$, $20_3$, $20_4$, etc. are continuously scanned. Specifically, an optical image of the sample 1 is acquired while the XY table 3 moves in the X direction. Then, images with the scan width W illustrated in FIG. 4 are continuously input to the photodiode array 105. After an image in the first frame $20_1$ is acquired, an image in the second frame $20_2$ is acquired. In this case, while the XY table 3 moves in a direction opposite to the direction in which the image in the first inspection frame 201 has been obtained, images with the scan width W are continuously input to the photodiode array 105. When the image in the third inspection frame $20_3$ is acquired, the XY table 3 moves in a direction opposite to the direction in which the image in the second inspection frame $20_2$ is acquired, that is, in the direction in which the image in the first inspection frame $20_1$ has been obtained. The diagonal portion of FIG. 4 schematically represents a region in which an optical image has been obtained as described above.

Next, the control unit B of FIG. 3 will be described.

In the control unit B, a control calculator 110 responsible for the overall control of the pattern evaluation apparatus 100 is connected to a position circuit 107, an image processing circuit 108, a map creating circuit 112, an autoloader control circuit 113, a table control circuit 114, a magnetic disk unit 109 as an example of a storage device, a magnetic tape device 115, a flexible disk device 116, a CRT (Cathode Ray Tube) 117, a pattern monitor 118, and a printer 119 via a bus 120 used as a data transmission path. The image processing circuit 108 corresponds to an optical image processing unit in the present invention. The map creating circuit 112 corresponds to a map creating unit in the present invention The XY table 3 is driven by an X-axis motor and a Y-axis motor controlled by the table control circuit 114. As for these motors, a linear motor may be used, as one example.

As above mentioned, optical acquisition unit A of FIG. 3 acquires an optical image (measurement data) of the sample 1. A specific example of a method of obtaining the optical image (measurement data) of the sample 1 will be described as follows.

A sample 1 is placed on a Z table (not illustrated) movable in a vertical direction. The Z table can be moved in a vertical direction by the XY table 3. More specifically, the XY table 3 is driven by the table control circuit 114 under the control of the control calculator 110 and can be moved by a drive unit that drives the XY table 3 in the X and Y directions. The position of the movement of the XY table 3 is measured by the laser length measurement unit 122 and sent to the position circuit 107. The sample 1 on the XY table 3 is automatically conveyed from the autoloader 130 driven by the autoloader control circuit 113, and the sample 1 is automatically discharged after the completion of the evaluation.

The light source 5 illuminates light for evaluating to the sample 1. The light emitted from the first light source 5 is transmitted through the lens 6 and the direction of the light is changed by the mirror 7, and thus, is focused on the sample 1 by the lens 8. The distance between the lens 8 and the sample 1 can be adjusted by moving the Z table in the vertical direction.

Light illuminated from the light source 5 and transmitted through the sample 1 is imaged as an optical image on the photodiode array 105 through the lens 104.

A procedure of acquiring the optical image in the evaluation region of the sample 1 is as described above using FIG. 4. An image of a pattern imaged on the photodiode array 105 of FIG. 3 is photoelectrically converted by the photodiode array 105 and further A/D (analogue/digital) converted by the sensor circuit 106. Image sensors are arranged in the photodiode array 105. As for the image sensors according to the present embodiment, a line sensor, in which CCD cameras as imaging devices are arranged in a row, can be used, as one example. The line sensor includes a TDI (Time Delay Integration) sensor. A pattern of the sample 1 is imaged by the TDI sensor while the XY table 3 continuously moves in the X-axis direction.

The optical image thus acquired is sent to the image processing circuit 108 of FIG. 3.

In the image processing circuit 108, pixel data in the optical image is represented by the gradation value of each pixel. For example, any gradation values of between 0 to 255, from a gray scale having 256 stages of gradation values is allocated to each pixel. Further, the region to be evaluated of the sample 1 is divided into predetermined unit regions, and the average gradation value in each unit region is obtained. The predetermined unit region may have a size of 1 mm×1 mm, as one example.

The gradation value obtained in the image processing circuit 108 and the average gradation value in each unit region are sent to the map creating circuit 112.

In the map creating circuit 112, the average gradation value is associated with an average value of the line width of a pattern. Moreover, the deviation of the gradation value in each unit region is associated with the roughness of the pattern edge. For example, for a predetermined pattern, the value of the line width measured by the dimension SEM and the gradation value of the optical image of the pattern are obtained to thereby establish the relational formula between the line width and the gradation value. The relational formula is stored in the map creating circuit 112. A user can convert the average gradation value obtained in the image processing circuit 108 into the average value of the line width in the unit region, using the relational formula. The deviation of the gradation value, that is, the standard deviation of the gradation value can be converted into the roughness of the pattern edge based on the relational formula.

Subsequently, the map creating circuit 112 creates the map representing at least one of the distribution of the average value of the line width and the distribution of the roughness of the pattern edge. The created map is stored in the magnetic disk unit 109, as one example of storage location.

Figure 5:
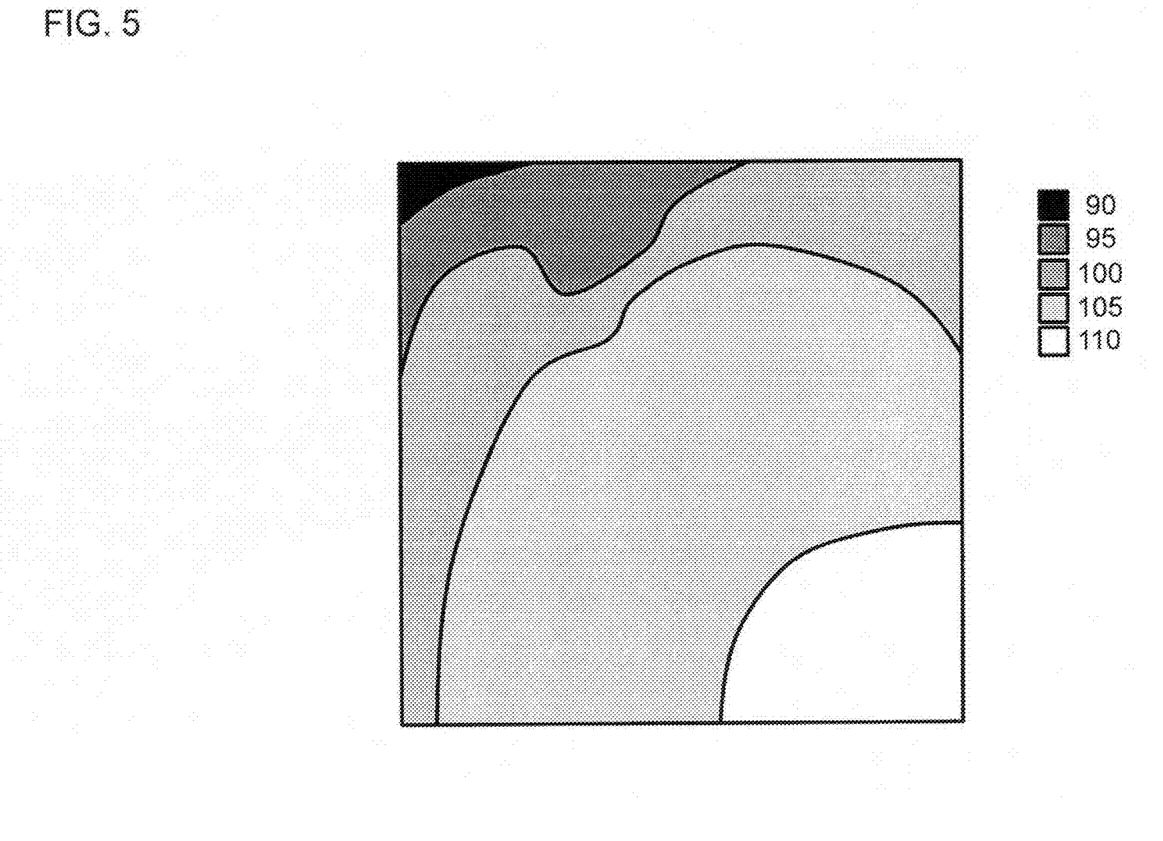
FIG. 5 shows an example of the line width distribution map of the line-and-space pattern.

FIG. 5 shows an example of the line width distribution map of the line-and-space pattern. The numerical values in FIG. 5 are the gradation values. In this case, a region having a gradation value of 100 corresponds to the region of a pattern having a line width equal to a design value. A region having a gradation value of 90 corresponds to the region of a pattern having a line width narrower by 2 nm than the design value. A region having a gradation value of 110 corresponds to the region of a pattern having a line width wider by 2 nm than the design value. Namely, in this example, the closer to the upper left of the pattern, the narrower the line width, and the closer to the lower right, the wider the line width.

Figure 6:
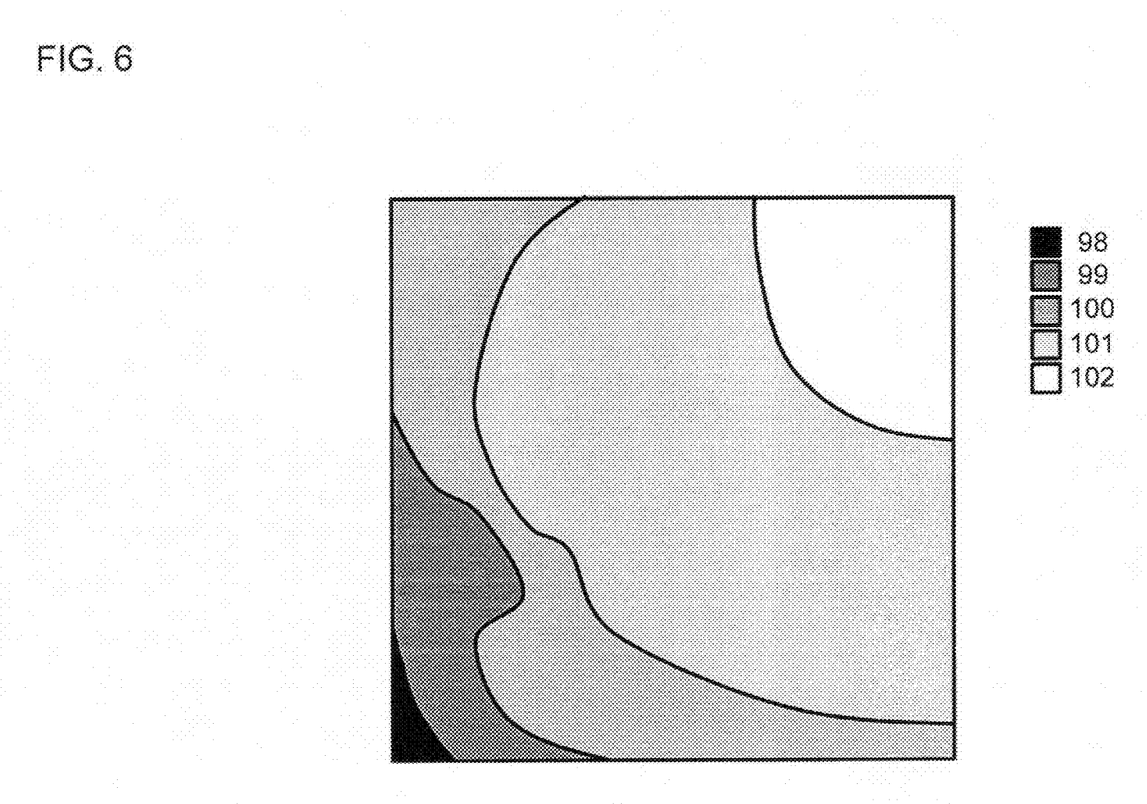
FIG. 6 shows an example of the distribution map of the roughness of the pattern edge of the line-and-space pattern.

FIG. 6 shows an example of the distribution map of the roughness of the pattern edge of the line-and-space pattern. The numerical values in FIG. 6 are the gradation values. In this case, a region having a gradation value of 98 corresponds to a region where the standard deviation of the gradation value is 2 nm. A region having a gradation value of 102 corresponds to a region where the standard deviation of the gradation value is 3 nm. Namely, in this example, the closer to the lower left or upper right of the pattern, the larger the roughness of the pattern edge.

As described above, the degree of the uniformity of the pattern in the sample 1 can be acquired from the map created in the map creating circuit 112 of FIG. 3. When it is determined that the line width and the roughness of the pattern edge are significantly varied, the data stored in the magnetic disk unit 109 can be fed back to further improve the conditions of photolithography upon formation of the pattern of the sample 1. The exposure conditions and the etching conditions for the resist are optimized based on the data, whereby the variation can be reduced.

The pattern evaluation apparatus according to the present embodiment may include other well-known components required for the evaluation of the sample 1 in addition to the constituent elements illustrated in FIG. 3.

Further, an inspection function can be incorporated into the pattern evaluation apparatus according to the present embodiment. For example, a pattern generating circuit, a reference circuit, and a comparing circuit can be incorporated into the configuration of FIG. 3.

Figure 7:
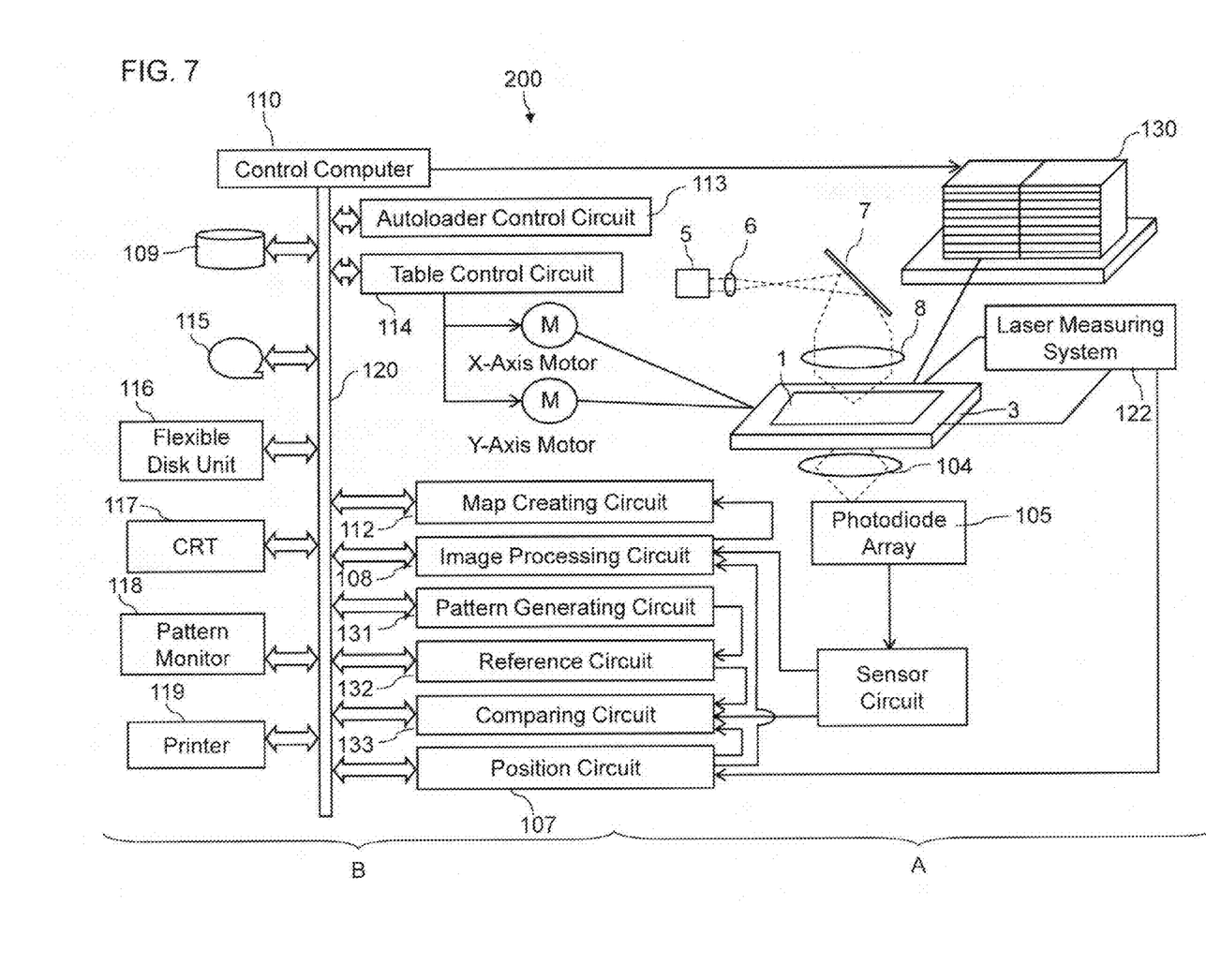
FIG. 7 is a diagram of the pattern evaluation apparatus including the pattern generating circuit, reference circuit, and comparing circuit.

FIG. 7 shows a pattern evaluation apparatus including a pattern generating circuit, reference circuit, and a comparing circuit. In FIG. 7 the same reference numbers as used in FIG. 3 have been used.

In the pattern evaluation apparatus 200 of FIG. 7, inspection using a die-to-database method can be performed. In this method, a reference image is generated based on design pattern data and compared with an optical image obtained by imaging a pattern.

In FIG. 7, design pattern data that is used as reference data in die-to-database inspection, is stored in the magnetic disk unit 109. This data is read out and sent to the pattern generating circuit 131, when necessary, in the course of the inspection process. In the pattern generating circuit 131, the design pattern data is converted into image data (design pixel data). After that, the image data is sent to the reference circuit 132 and used in the generation of a reference image. The generated reference image is sent to the comparing circuit 133, the optical image is also sent from the sensor circuit 106 to the comparing circuit 133. In the comparing circuit 133 the optical image sent from the sensor circuit 106 and the reference image generated in the reference circuit 132 are compared with each other using an appropriate comparative determination algorithm. When an error exceeds a predetermined value, the corresponding portion is determined as a defect. Subsequently, the coordinates of the defect and the optical image and the reference image as a basis for the defect determination are stored in the magnetic disk unit 109.

The defect determination can be performed by the following two kinds of method. In one of the methods, when a difference exceeding a predetermined threshold size is observed between a position of a contour line in the reference image and a position of a contour line in the optical image, it is determined that there is a defect. In the other method, when a ratio of a line width of a pattern in the reference image to a line width of a pattern in the optical image exceeds a predetermined threshold value, it is determined that there is a defect. In this method, a ratio of a distance between patterns in the reference image and a distance between patterns in the optical image may be used.

In a die-to-database method, a reference image compared with an optical image to be inspected, as above mentioned, is a reference image created based on design pattern data. However, the pattern evaluation apparatus according to the present invention can be applied to the inspection method according to the die-to-die method, and a reference image in this case is an optical image different from the optical image to be inspected.

Moreover, the pattern evaluation apparatus according to the present embodiment can include a review function, in addition to an inspection function. The term "review" as used herein, refers to an operation performed by the operator to determine whether a detected defect can be tolerated.

For example, the coordinates of the portion determined as a defect in the comparing circuit 133 of FIG. 7 and the optical image and the reference image as the basis for the defect determination are sent to a review device (not illustrated). The operator compares the reference image as the basis for the defect determination with the optical image including the defect, and then performs the review. Specifically, the observation optical system of the pattern evaluation apparatus 200 (the light source 5, the lenses 6, 8, 104, the mirror 7, the photodiode array 105, and the sensor circuit 106) shown in FIG. 7 is used to display the image of the defective portion of the sample 1. At the same time, the conditions of the defect determination, and the optical image and the reference image as the basis of the defect determination are displayed using the screen of the control calculator 110 illustrated in FIG. 7. The defect information obtained through the review process is stored in the magnetic disk device 109 of FIG. 3.

When at least one defect to be modified is confirmed in the review, the sample 1 with a defect information list is sent to a modification apparatus (not shown) as an exterior apparatus of the pattern evaluation apparatus 200. Since a modification method is different depending on whether the type of the defect is a protrusion-type defect or a recess-type defect, the types of the defect including the distinction between the protrusion type and the recess type and the coordinates of the defect are included with a defect information list.

In the above example, although the line-and-space pattern is described as an example of a repeated pattern, the present invention is not limited thereto. The present invention is applicable to repeated patterns such as a hole pattern.

For example, when a hole pattern having a hole diameter smaller than the resolution limit of the observation optical system is formed on a sample, if there are the edge roughness and the shape defect due to a lack in the pattern, the regularity of the pattern is disturbed, so that a gradation value of a portion having the shape defect is different from the gradation values of the periphery of the portion. On the other hand, when there is no shape defect and regular patterns are repeated, the gradation value of an optical image is uniform. Such a change of the gradation value is also found in the shape defect due to abnormality in the hole diameter in the pattern and the gap abnormality between a target pattern and a pattern adjacent thereto due to the pattern positional deviation.

Accordingly, the region to be evaluated of a sample is divided into predetermined unit regions to examine the deviation of the gradation value in each unit region, whereby the shape defect due to the edge roughness and the lack in a pattern can be detected. The predetermined unit region may have a size of 1 mm×1 mm, as one example.

The shape defect due to the abnormality in the hole diameter in the pattern and the gap abnormality between a target pattern and a pattern adjacent thereto due to the pattern positional deviation can be detected by comparing the average gradation values in each unit region with each other. When each diameter and gap of the hole are uniform, the average gradation value in each unit region is a uniform value. On the other hand, for example, when some hole diameters are small, a difference occurs between the average gradation value of the unit region where the abnormality in the hole diameter occurs and the average gradation value of the unit region having a normal hole diameter. Moreover, when a distance between patterns deviates by the occurrence of the pattern positional deviation, a difference occurs between the average gradation value of such a unit region and the average gradation values of other unit regions.

In the pattern evaluation apparatus 100 shown in FIG. 3, when the sample 1 having a hole pattern is evaluated, an optical image of the pattern is sent to the image processing circuit 108. In the image processing circuit 108, pixel data in the optical image is represented by the gradation value of each pixel. For example, any of gradation values 0 to 255 from a gray scale having 256 stages of gradation values is allocated to each pixel. Further, the region to be evaluated of the sample 1 is divided into predetermined unit regions, and the average gradation value in each unit region is obtained.

The gradation value obtained in the image processing circuit 108 and the average gradation value in each unit region are sent to the map creating circuit 112. In the map creating circuit 112, the average gradation value is associated with an average value of the hole diameter of a pattern. Moreover, the deviation of the gradation value in each unit region is associated with the roughness of the pattern edge. For example, for a predetermined pattern, the value of the line width measured by the dimension SEM and the gradation value of the optical image are obtained to thereby establish the relational formula between the hole diameter and the gradation value. The relational formula is stored in the map creating circuit 112. A user can convert the average gradation value obtained in the image processing circuit 108 into the average value of the hole diameter, using the relational formula. The deviation of the gradation value, that is, the standard deviation of the gradation value can be converted into the roughness of the pattern edge based on the relational formula. Subsequently, the map creating circuit 112 creates the map representing at least one of the distribution of the average value of the hole diameter and the distribution of the roughness of the pattern edge. The created map is stored in the magnetic disk unit 109, as one example.

As described above, the degree of the uniformity of the hole pattern in the sample 1 can be acquired from the map created in the map creating circuit 112. When it is determined that the hole diameter and the roughness of the pattern edge are significantly varied, the information can be fed back to the conditions of photolithography upon formation of the pattern of the sample 1. Specifically, the exposure conditions and the etching conditions for the resist are optimized so that the variation can be reduced.

As mentioned above, in the pattern evaluation method and apparatus according to the present embodiment, an observation optical system for acquiring an optical image of a sample, as light emitted from a light source, DUV (Deep Ultraviolet radiation) light can be used. Accordingly, the evaluation can be performed without inducing reduction in throughput in comparison with a case where EB (Electron Beam) is used as a light source.

In the case of using the DUV light, even if the size of a pattern formed on a sample is smaller than the resolution limit of the observation optical system, the shape defect can be detected according to the pattern evaluation method and the pattern evaluation apparatus according to the present embodiment. Namely, a region to be evaluated is divided into predetermined unit regions, and the average gradation values in the unit regions are compared with each other, whereby the line width and the gap abnormality in the pattern having a size smaller than the resolution limit of the observation optical system can be detected. Moreover, the deviation of the gradation value in each unit region is examined, whereby the roughness of the pattern edge and the lack in a pattern can be detected.

Further, according to the present embodiment, the relationship between the shape defect and the gradation value is previously acquired, and then the gradation value obtained from an optical image is converted into a specific dimension to create a dimension map, whereby the degree of the uniformity of a pattern on a sample can be acquired. Based on such a map, if the degree of variation in the pattern is not less than a predetermined value, when this information is fed back to the conditions of photolithography upon pattern formation, the variation can be reduced.

The features and advantages of the present invention may be summarized as follows According to the first embodiment, a pattern evaluation method is provided which can evaluate a fine pattern with high accuracy without reducing throughput.

According to the second embodiment, a pattern evaluation apparatus is provided which can evaluate a fine pattern with high accuracy without reducing throughput.

The present invention is not limited to the embodiments described above and can be implemented in various modifications without departing from the spirit of the invention.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all pattern evaluation methods and pattern evaluation apparatuses employing the elements of the invention and variations thereof, which can be designed by those skilled in the art.

What is claimed is:

1. A pattern evaluation method comprising the steps of:
    illuminating light from a light source constituting an optical system and acquiring an optical image of a sample having a repeated pattern with a period not more than a resolution of the optical system;
    allocating a gradation value to each pixel of the optical image and obtaining at least one of an average gradation value for each predetermined unit region and deviation of the gradation value in the unit region; and
    performing at least one of a process of converting the average gradation value into average line width information in the unit region of the repeated pattern and a process of converting the deviation of the gradation value into roughness of the repeated pattern and creating a map representing distribution of at least one of the average line width information and the roughness with the use of an obtained converted value.

2. The pattern evaluation method according to claim 1, wherein a wavelength of the light is longer by twice or more than a pitch of the repeated pattern.

3. The pattern evaluation method according to claim 1, wherein the light is deep ultraviolet radiation.

4. The pattern evaluation method according to claim 1, wherein the repeated pattern is a line-and-space pattern, and the average line width information is an average value of a plurality of widths of a line of the line-and-space pattern.

5. The pattern evaluation method according to claim 1, wherein the repeated pattern is a line-and-space pattern, and the roughness is a line edge roughness which is a size of irregularities on sidewalls of the line.

6. The pattern evaluation method according to claim 1, wherein the repeated pattern is a line-and-space pattern, and the design width of a line is not more than 40 nm.

7. A pattern evaluation apparatus comprising:
    an optical image acquiring unit which acquires an optical image of a pattern, which is a target to be evaluated, with the use of an image sensor;
    an optical image processing unit which allocates a gradation value to each pixel of the optical image and obtains at least one of, an average gradation value for each predetermined unit region, and deviation of the gradation value in the unit region; and
    a map creating unit which performs at least one of a process of converting the average gradation value into average line width information in the unit region of the pattern and a process of converting the deviation of the gradation value into roughness of the pattern and creates a map representing distribution of at least one of the average line width information and the roughness, using an obtained converted value,
    wherein the optical image acquiring unit comprises a light source illuminating light to the pattern and a lens focusing light from the light source, transmitted through or reflected by the pattern, on the image sensor, and
    a resolution limit determined by a wavelength of the light from the light source and the numerical aperture of the lens is a value that does not resolve the pattern.

8. The pattern evaluation apparatus according to claim 7, wherein the light from the light source has a wavelength longer by twice or more than a pitch of the pattern.

9. The pattern evaluation apparatus according to claim 7, wherein the light from the light source is deep ultraviolet radiation.

10. The pattern evaluation apparatus according to claim 7, further comprising a comparing unit which compares the optical image with a reference image and determines that there is a defect when a difference value between the optical image and the reference image exceeds a predetermined threshold value.

11. The pattern evaluation apparatus according to claim 10, wherein the reference image is a reference image created from design data of the pattern, the apparatus further comprising a reference image creating unit which creates the reference image, wherein the reference image created by the reference image creating unit is sent to the comparing unit.

* * * * *